(12) United States Patent
Mata

(10) Patent No.: US 6,342,054 B1
(45) Date of Patent: Jan. 29, 2002

(54) POSITIONING AND LOCKING DEVICE

(75) Inventor: Jacques Mata, Etoy (CH)

(73) Assignee: Stryker Trauma SA (CH)

( * ) Notice: Subject to any disclaimer, the term of this patent is extended or adjusted under 35 U.S.C. 154(b) by 0 days.

(21) Appl. No.: 09/473,588

(22) Filed: Dec. 28, 1999

(30) Foreign Application Priority Data

Dec. 29, 1998 (CH) .............................................. 2582/98

(51) Int. Cl.$^7$ .............................................. A61B 17/60
(52) U.S. Cl. .......................................... 606/59; 606/54
(58) Field of Search .............................. 606/56, 54, 55, 606/57, 58, 59

(56) References Cited

U.S. PATENT DOCUMENTS

| | | |
|---|---|---|
| 4,784,125 A | 11/1988 | Monticelli et al. |
| 5,047,029 A * | 9/1991 | Aebi et al. ................ 606/59 |
| 5,095,919 A | 3/1992 | Monticelli et al. ........... 606/56 |
| 5,741,252 A | 4/1998 | Mazzio et al. ............... 606/54 |
| 5,752,954 A | 5/1998 | Mata et al. ................ 606/59 |

FOREIGN PATENT DOCUMENTS

| | | |
|---|---|---|
| EP | 0 700 664 A1 | 3/1996 |
| EP | 0 704 192 A1 | 3/1996 |
| EP | 0 813 845 A1 | 12/1997 |
| WO | WO 88/01152 | 2/1988 |
| WO | WO 97/35527 | 10/1997 |

* cited by examiner

Primary Examiner—Cary E. O'Connor
(74) Attorney, Agent, or Firm—Lerner, David, Littenberg, Krumholz & Mentlik, LLP

(57) ABSTRACT

A device for positioning and locking rods, pins or wires, particularly for an external fixator in the field of orthopaedics is provided. The device comprises two jaw faces and a tightening assembly exhibiting a connecting element secured to a tightening member, the assembly allowing the jaws to form at least one opening exhibiting at least one cavity in the form of a gripping jaw allowing a hoop, a rod, a pin or a wire to be clipped by pressure against the action of an elastic member keeping the device in position prior to the locking action which is performed using the tightening member.

27 Claims, 4 Drawing Sheets

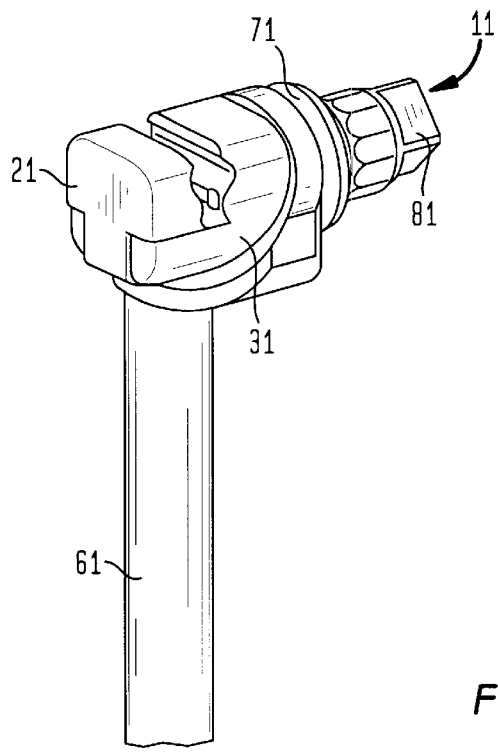
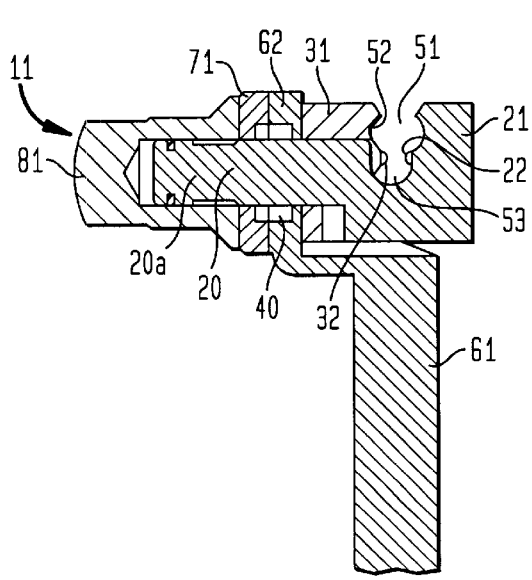
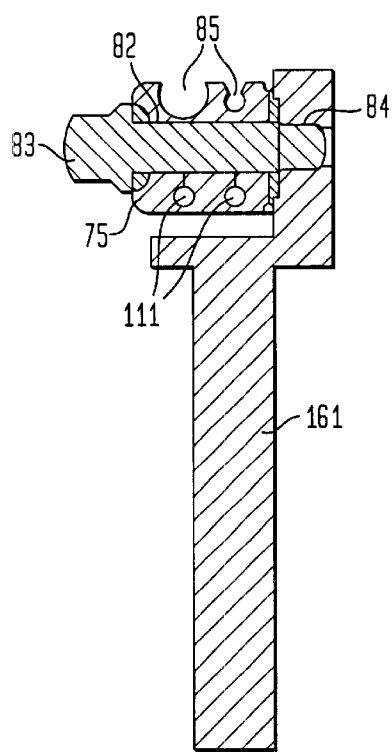

POSITIONING AND LOCKING DEVICE

BACKGROUND OF THE INVENTION

1. Field of the Invention.

The subject of the present invention is a device for positioning and locking rods, pins or wires, particularly for an external fixator in the field of orthopaedics. More particularly, it relates to a clamping device used as a support piece in osteosynthesis and osteoplasty to be incorporated into external fixator elements when a bone is fractured.

2. Description of Prior Art.

There are a great many support pieces or clamps on the market for producing fixation assemblies to meet the ever-increasing demands of orthopaedic surgery. Those selected should be those which are more able to fulfil their function through their simplicity and their ease of handling, time being an extremely important factor in such operations. Although external fixators have been in existence for some time, the support pieces are still evolving in order to provide better solutions for various problems often encountered.

U.S. Pat. Nos. 4,784,125 and 5,095,919 relate to a hoop element and also an external fixator in which this hoop element is incorporated with the members for fixing pins and wires intended to be used in osteosynthesis and osteoplasty.

European Patent EP 0 321 472 describes an articulation element for the relative positioning of fixing rods or bone pins of an external fixator. This articulation element comprises a number of pairs of gripping jaws which on the adjacent faces exhibit slots which form a passage intended to accommodate a rod or a pin. The angular position between the said pairs can be locked and there is a tightening element passing through the said pairs of gripping jaws to tightly clamp the rods or pins in a relative position. Furthermore, the gripping jaws which form a pair are equipped respectively with a positioning projection and with a cutout of a complementing shape.

U.S. Pat. No. 5,752,954 relates to an articulation device for components of an external fixator. This device allows for the relative positioning of fixing rods or pins and comprises two pairs of gripping jaws arranged in such a way that an elastic element acts against the gripping jaws and press the adjacent faces of the gripping jaws in order to lock the articulation device. In their adjacent faces, the gripping jaws have slots which are positioned and arranged in such a way to exhibit an opening allowing a rod or pin to be clamped by pressure. The teachings of U.S. Pat. No. 5,752,954 are incorporated herein by reference.

The holding and clamping devices known from the prior art have the disadvantage of not holding themselves in a chosen position when they are attached to rods, bars or pins. The user therefore has to maintain the correct relative positioning of the rods, pins and wires until such time as he performs the tightening or locking operation.

SUMMARY OF THE INVENTION

The object of the present invention is to overcome this drawback and to provide a device which holds itself in its assembled position, which can be adjusted, until such time as the assembly is tightened or locked.

The present invention corresponds to a device for positioning and locking rods, pins or wires, particularly for an external fixator in the field of orthopaedics. The device comprises two external jaws and a tightening assembly. The tightening assembly has a connecting element secured to a tightening member. The assembly allows the jaws to form at least one opening exhibiting at least one cavity in the form of a gripping jaw allowing a hoop, a rod, a pin, bar or a wire to be clipped by pressure against the action of an elastic member which keeps the device in position prior to the locking action which is performed using the tightening member.

According to one embodiment, the connecting element is a bushing which passes through the two jaws and can have placed inside it a retained rod which is designed to be locked with the jaws by the tightening member. The elastic member is a spring in the form of a staple connecting the two jaws, at the opposite side of which is the clipping or gripping zone which has the opposing clamping faces; it may be a single or double spring. The free ends of the staple forming the spring are introduced into orifices in the jaws. According to another embodiment, the elastic member is an axial tension or coil spring. In both embodiments, the two jaws have assembly notches which position them relative to one another.

The jaws and the bushing have devices which prevent one from rotating relative to the other. The upper jaw member has a conical recess and a cylindrical bore for accommodating the bushing, the lower jaw having a bore which has two opposed flat surfaces to play a part in mating with the bushing, the latter having two opposed flat surfaces in its central part in the direction of its axis which correspond with those of the lower jaw member to make it easier to fit into the said lower jaw face.

The bushing, which is cylindrical, has an upper part in the form of a truncated cone with slots in the direction of its axis to allow the rod to be clamped tightly once it has been placed inside it. The bushing has its lower part threaded with a diameter appropriate to that of the tightening nut.

According to another embodiment, the connecting element is a shank passing through a ring connected to a rod, the upper jaw being placed at one of the ends of the shank, around which the lower jaw and the tightening nut are positioned.

According to this same embodiment, the two jaws exhibit an opening in the form of a gripping jaw with at least one cavity allowing a pin or a wire to be clipped and then clamped within the jaws. The two jaws have balls made of a hard material placed alternately between the cavities to assist with locking the wire housed inside it.

The nut is advantageously produced in the form of a ribbed knob screwed around the lower part of the shank which allows the entire device to be kept assembled. A toothed annulus is inserted between the ribbed or knurled knob and the post to set the angular position of the device which will thereafter remain locked once the ribbed knob has been tightened. The device comprises an axial helical spring between the ring and the toothed annulus.

According to a third embodiment, the connecting element is in the form of a bolt, the free end of which is threaded to screw into a bore in the post, the bolt passing through a clamp delimiting at least one gripping jaw in the form of a slot placed transversely with respect to the connecting element, the material placed between the bottom of the slot and the external surface of the clamp acting as a spring.

According to any one of the embodiments, the device is able to act as a support piece for an external fixator comprising a circular or part circular hoop formed from a bar of specified cross-sections, pins, bars or wires or rods, in which fixator the devices exhibit outer openings allowing the clipping of the hoop, of the pins and of wires and the fixing of the rods or of the said devices by their posts so that by tightening the devices, it is possible to achieve relative positioning thereof prior to locking.

BRIEF DESCRIPTION OF THE DRAWINGS

The drawing illustrates, by way of examples, some embodiments of the device with a clipping gripping jaw according to the invention.

FIG. 4 is a perspective view of another embodiment of the device;

FIG. 5 is a cross-sectional view through the device of FIG. 4;

FIG. 8 is a cross-sectional view through the device according to a third embodiment of the invention.

DESCRIPTION OF THE PREFERRED EMBODIMENTS

Figure 1:
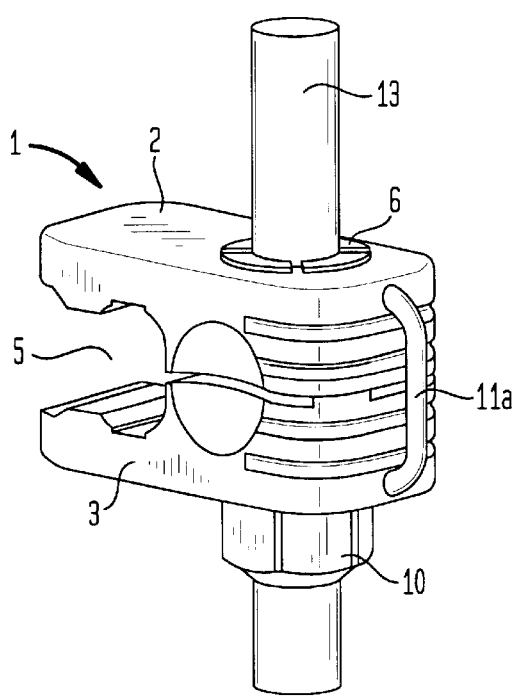
FIG. 1 is a perspective view of a first embodiment of the device of the present invention.
Figure 2:
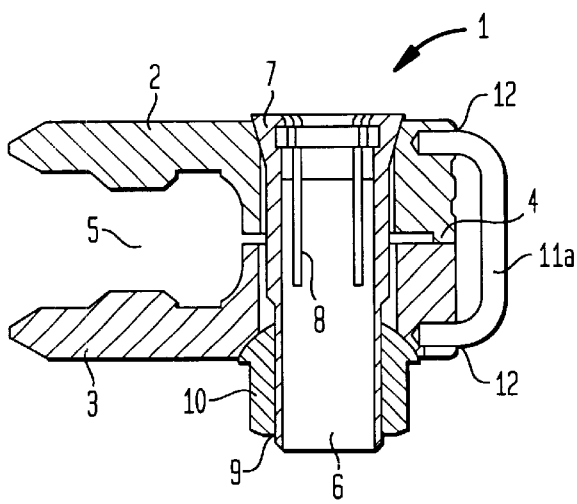
FIG. 2 is a cross-sectional view through the device of FIG. 1.
Figure 3:
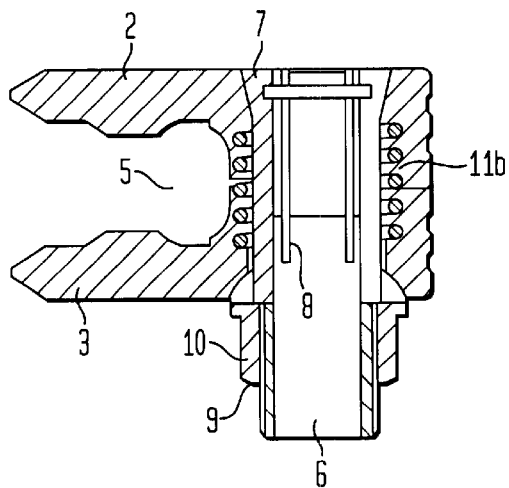
FIG. 3 is a section through the device of FIG. 1 with an alternative form of elastic member.

Referring to FIGS. 1 and 2, the positioning and locking device, generally denoted as 1 is made up of an upper jaw member 2 and a lower jaw member 3 having opened faces which are machined with assembly notches 4 to allow one to be positioned and pivoted against the other, leaving an opening 5 at the opposite end. A bushing or hollow shaft 6 passes through the two jaws 2, 3 at right angles, through the opposite end of the jaws with respect to the gripping jaw opening. As best seen in FIGS. 2 and 3, bushing 6, at its upper part 7, has the shape of a cone frustum with slots 8 which start from this upper part 7 and run in the direction of the axis of the bushing to end about halfway down the length thereof. The lower part of bushing 6 is threaded at 9 and is screwed into a nut 10 which clamps the two jaws 2, 3 together.

A spring in the form of a staple 11a or bent wire is housed inside holes 12 each made in each one of the jaws 2, 3 also on the opposite side to the opening of the gripping jaw. Upper jaw 2 has a conical recess in its upper part and a cylindrical bore to accommodate bushing 6 and lower jaw 3 has a bore which has two opposed flat surfaces to play a part in holding bushing 6 in place especially against rotation, these flat surfaces not being depicted in the drawing. Bushing 6 has a smaller diameter in its threaded lower part 9 and in its central part has two opposed flat surfaces, not shown in the drawing, which engage the flats on lower jaw 3 to prevent bushing 6 from rotating relative to the jaws and allow the nut to be locked.

Between bushing 6 and the bores of jaw 2, 3 there is a clearance that allows the jaws device 1 to be pivoted outwardly against the face of staple spring 11a, prior to the tightening operation. The clearance allows the jaws 2, 3 to be parted just enough for clipping an element between the faces of each jaw, for example, onto a rod or a hoop along which device 1 can slide and therefore change position. A rod 13 may be inserted into bushing 6 and locked in position by the clamping action of the conical position of the upper part of bushing 6 which deforms inwardly as nut 10 is tightened pulling the bushing downwardly into the conical recess of upper jaw 2. This causes upper part 7 of bushing 6 to deform inwardly in the area of slots 8. This rod 13 may remain fixed in a concrete assembly position so that one can adjust the relative positions of all the elements of the device prior to the final operation of tightening the assembly.

FIG. 3 shows in section the device of FIGS. 1 and 2 in which the elastic member is now an axial tension spring 11b which, in its equilibrium portion, keeps the two jaws 2, 3 assembled, allowing them to open during the clipping operation and holding the device locked until final tightening is performed using the nut 10.

Figure 6:
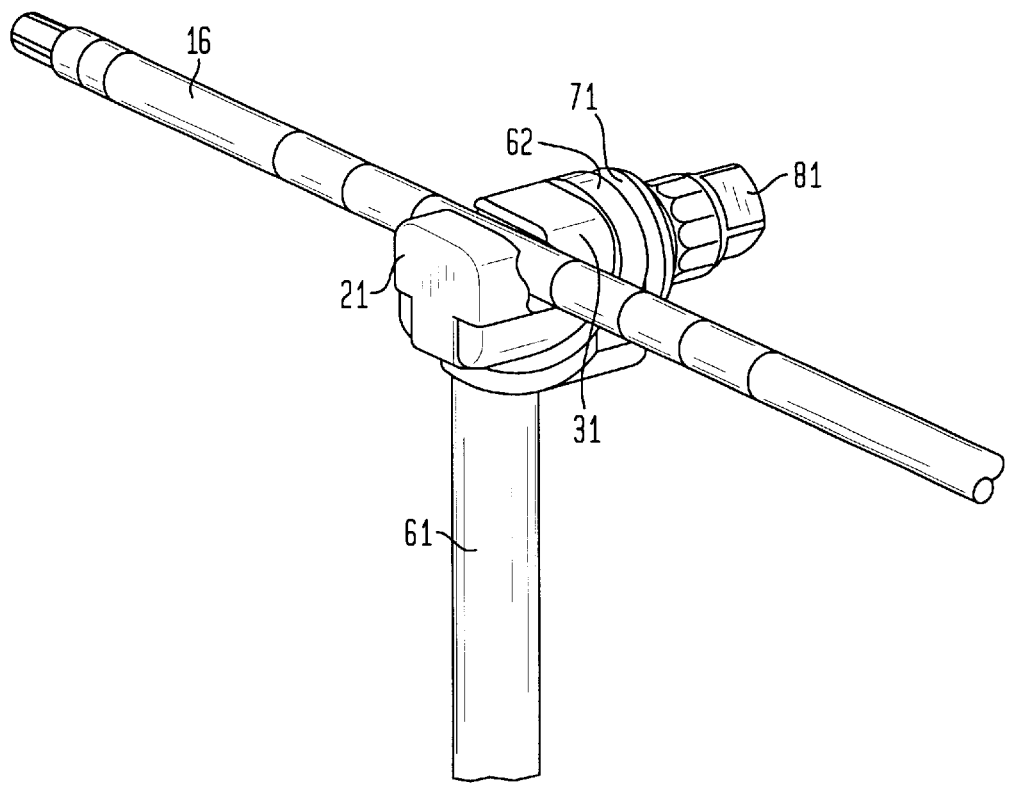
FIGS. 6 and 7 show the device of FIG. 4 holding respectively a pin and a wire in its gripping jaw.
Figure 7:
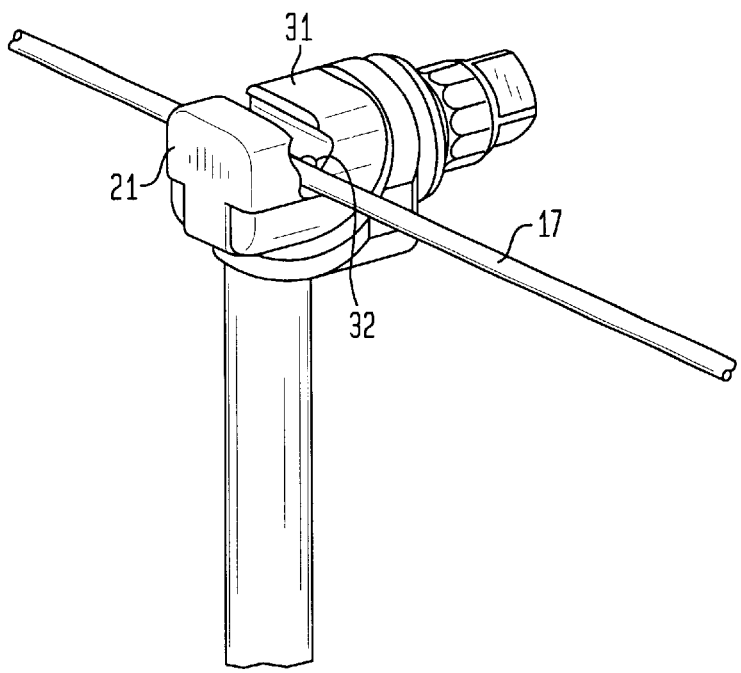

Referring to FIGS. 4 to 7, there is shown another embodiment in which the device 11 consists of a tie bolt 20, which at one of its ends has an upper jaw member 21 with balls 22 made of a material which is harder than the piece being clamped, these balls being made, for example, of ceramic or of a hard metal. Placed around the tie bolt 20 in succession are a lower jaw member 31 with other balls 32 made of any material that is harder than the piece to be held, the two jaw 21, 31 creating an outer opening 51 with two cavities 52, 53; a spiral spring 40, a post 61 ending in a ring 62 at one of its ends. Ring 62 may have teeth arranged therearound for engaging a toothed plate 71. A nut in the form of a ribbed knob 81 is threaded onto end 20a of the bolt 20. FIGS. 6 and 7 show how the device 11 clips a pin 16 in its outer cavity 52 or a wire 17 in its inner cavity 53.

FIG. 8 shows a third embodiment with a nut 82 as its connecting element. The part 75 is a clamp with sets of gripping jaws with openings 85, in which pins or wires can be clipped. The elastic element may be incorporated into the clamp and may be in the form of a thin piece of material located away from the openings and acting as a spring. The elastic element may be in the form of a narrow slit between adjacent jaw faces terminating in a small through bore 111 adjacent to the bottom of part 75. As the bolt 82 is tightened in threaded bore 84 of post 161, the narrow slit is closed with the thin metal of clamp 75 around bores 111 acting as a spring.

According to the first embodiment, bushing 6 which passes through two jaws 2, 3 is fitted into upper jaw 2 with the aid of the cone frustum shape of its upper part, which rests against the similarly shaped recess of the upper jaw. The rod 13 is inserted into bushing 6 to finally be tightened using nut 10. This nut has a large head to make it easier to tighten by hand before being locked using any appropriate tool when the system is in place. Device 1 with rod 13 in place is clipped via its outer opening 5 by lateral pressure onto a hoop or bar 91 and remains in this position by virtue of the action of the spring 11a, 11b. It goes without saying that any other form of opening is envisageable without departing from the scope of the present invention, to allow the device to be clipped onto any other part, not depicted.

According to the second embodiment, the two jaws 21, 31 use lateral pressure to clip a pin 16 or a wire 17 respectively in the outer cavity 52 or inner cavity 53, against the face of the spring 40. This spring is a spiral spring which, pressing against the ribbed knob 81, presses the lower jaw cheek 31 against the upper jaw cheek 21; the balls 22, 32 positioned in an offset configuration, retain the wire so that this wire cannot escape from the gripping jaw. The ribbed knob 81 presses the device-pin or device-wire assembly together and once the post 61, which has one end in the form of a ring 62, has been orientated into its final position, clamps it against the toothed plate 71 so that it remains locked. The ribbed knob 81 has square head, but it goes without saying that any other shape of head may be used without departing from the scope of the present invention. As in the first embodiment and for the same reason, it has a large head to make it easier to initially tighten it by hand before finally locking it when the system is in place.

Figure 9:
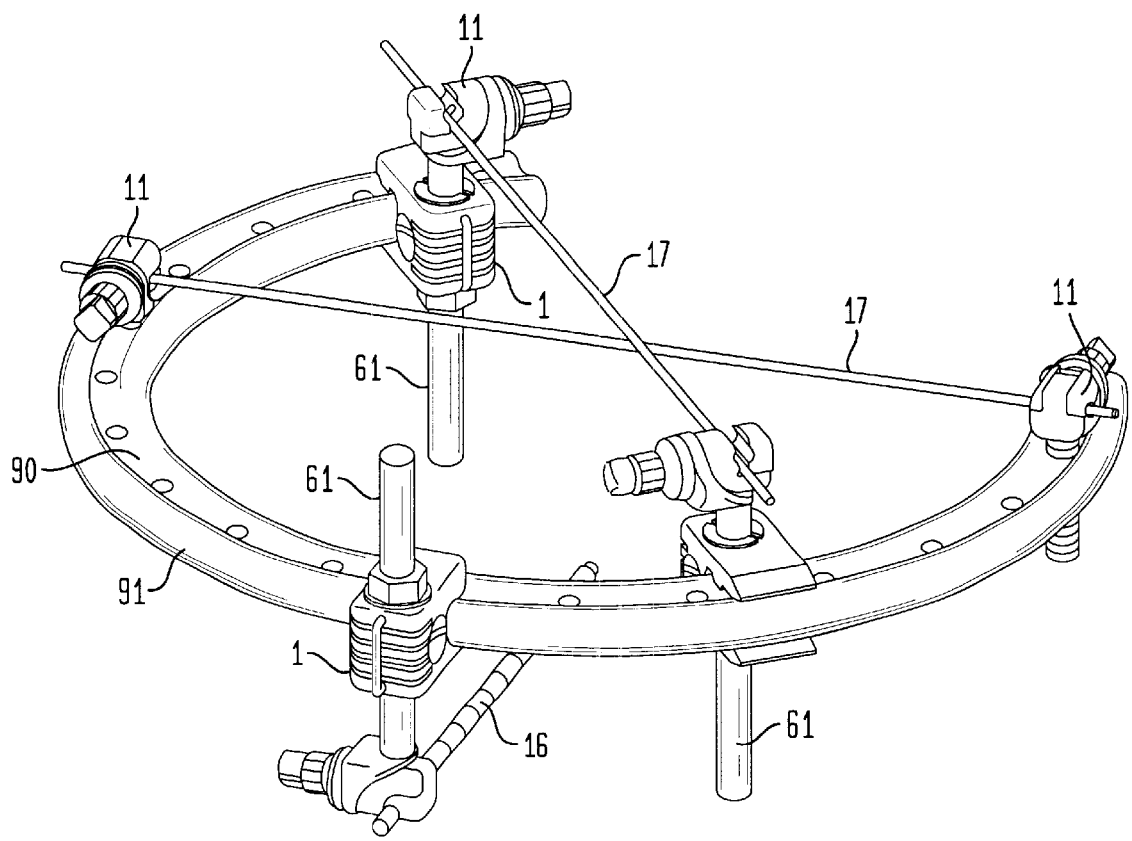
FIG. 9 shows part of an external fixator for osteosynthesis and osteoplasty, in which a series of devices with clipping or gripping jaws of the present invention are shown as support pieces for positioning rods, pins and wires cooperating with a hoop.

FIG. 9 depicts a hoop, bar or ring element 91, without a complete circle being formed, which forms part of an external fixator 90. The hoop element has a section with a web at the center of rectangular overall shape which serves as an element for connecting to two lateral reinforcements of cross section that is symmetrical with respect to an axis perpendicular to the web, allowing the support pieces to be clipped onto the inside or onto the outside of the hoop, as required. This figure shows three devices with clipping type gripping jaws according to the first embodiment 1 which are clipped, two to the inside of the hoop, and the third to its outside. In all three instances, devices 1 are assembled with other devices 11 according to the second embodiment to show how the two embodiments 1, 11 according to the invention can collaborate with each other, post 61 of one of them becoming rod 13 of the other. Two pairs of devices 11 support two transfixing wires which pass right through a bone (not shown), a third holds a pin 16 which would also be inserted into another part of the bone. The combination of these elements, the hoop with pins, wires, rods and devices with clipping gripping jaws makes it possible to achieve relative positioning of items with respect to each other, tightening it by hand to thereafter lock it permanently while maintaining the relative positions between the various elements. The device of FIG. 9 may also be assembled using a second hoop 91.

What is claimed is:

1. A device for positioning and locking rods, pins or wires, particularly for an external fixator in the field of orthopedics, comprising two jaw members and a tightening assembly, the tightening assembly has a connecting element secured to a tightening member, the jaws members having faces forming at least one opening exhibiting at least one cavity in the form of a gripping jaw allowing a hoop, a rod, a pin or a wire to be clipped by pressure against the action of a spring force which keeps the hoop, rod, pin or wire in position prior to the locking action which is performed using the tightening member wherein the connecting element is a bushing which passes through the two jaws and includes a rod which is designed to be locked with the jaws by the tightening member.

2. The device according to claim 1, wherein the spring force is generated by an external spring connecting the two jaws.

3. The device according to claim 2, wherein the spring is in the form of at least one staple fixed to each jaw at an end opposite the jaw part at the gripping area.

4. The device according to claim 2, wherein the free ends of the staples forming the spring are introduced into orifices made in the jaw members.

5. The device according to claim 1, wherein the spring force is generated by an axial tension spring.

6. The device according to claim 1, wherein the two jaws have assembly notches which position them relative to one another.

7. The device according to claim 1, wherein the two jaws and the bushing have mating members which prevent one from rotating relative to another.

8. The device according to claim 1, wherein the upper jaw has a conical recess and a cylindrical bore for accommodating the bushing, the lower jaw having a bore which has two opposed flat surfaces to play a part in mating with the bushing, said bushing having two opposed flat surfaces in its central part in the direction of its axis which correspond with those of the lower jaw.

9. The device according to claim 1, wherein the bushing has an upper part in the form of a cone frustum with slots in the direction of its axis to allow a rod to be clamped tightly once it has been placed inside the cone.

10. The device according to claim 1, wherein the bushing has a lower threaded part and a diameter that allows it to cooperate with a tightening nut.

11. The device according to claim 1, for receiving a hoop intended to retain pins, wires and/or rods so as to form an external fixator.

12. A clamp for attaching a bone fixation element to an external frame comprising:
   a pair of jaw members having a bore therethrough with a conical surface surrounding said bore adjacent an outer surface of a first of said jaw members;
   a hollow bushing in said bore having a first split conical end engageable with said conical surface surrounding said bore and having a second threaded end extending through the second of said jaw members;
   a post having a bone fixation element mounted thereon slidably received in the hollow portion of said bushing; and
   a nut engageable with said threaded portion of said bushing for forcing said conical surfaces together to lock said post in position.

13. The clamp as set forth in claim 12, further including an elastic member acting between said pair of jaws generating a spring force to move adjacent faces of said jaw members towards one another.

14. The device according to claim 13, wherein the elastic member is an external spring connecting the two jaws.

15. The device according to claim 14, wherein the spring is in the form of at least one staple fixed to each jaw at an end opposite the jaw part at the gripping area.

16. The device according to claim 15, wherein the free ends of the staples forming the spring are introduced into orifices made in the jaw members.

17. The device according to claim 13, wherein the elastic element is an axial tension spring.

18. The clamp as set forth in claim 12, wherein said jaws have adjacent faces with engaging surfaces which prevent the rotation of said jaw members with respect to one another.

19. The device according to claim 18, wherein the two jaws have assembly notches which position them relative to one another.

20. The device according to claim 18, wherein the two jaws and the bushing have mating members which prevent one from rotating relative to another.

21. A device for positioning and locking rods, pins or wires, particularly for an external fixator in the field of orthopaedics, comprising two jaw members and a tightening assembly, the tightening assembly has a connecting element secured to a tightening member, the jaws members having faces forming at least one opening exhibiting at least one cavity in the form of a gripping jaw allowing a hoop, a rod, a pin or a wire to be clipped by pressure against the action of a spring force which keeps the hoop, rod, pin or wire in position prior to the locking action which is performed using the tightening member wherein the connecting element is a shank passing through a ring connected to a rod, the upper jaw member being placed at one of the ends of the shank around which the lower jaw and the tightening member are positioned.

22. The device according to claim 21, wherein the two jaws form an opening in the form of a gripping jaw with at least one cavity allowing a pin or a wire to be clipped.

23. The device according to claim 22, wherein, on at least one of the two jaw members, balls made of a hard material are placed alternately between at least first and second cavities to assist with locking a wire housed in a first cavity of the gripping jaw, the second cavity of the two jaw members being intended to accommodate a pin.

24. The device according to claim 21, wherein the tightening member is a nut in the form of a ribbed knob screwed around the lower part of the shank, keeping the device assembled.

25. The device according to claim 21, wherein a toothed annulus is inserted between the ribbed knob and the post to set the angular position of the device.

26. The device according to claim 21, further comprising a helical spring between the ring and the toothed annulus.

27. A device for positioning and locking rods, pins or wires, particularly for an external fixator in the field of orthopedics, comprising two jaw members and a tightening assembly, the tightening assembly has a connecting element secured to a tightening member, the jaws members having faces forming at least one opening exhibiting at least one cavity in the form of a gripping jaw allowing a hoop, a rod, a pin or a wire to be clipped by pressure against the action of an elastic member which keeps the hoop, rod, pin or wire in position prior to the locking action which is performed using the tightening member, wherein the connecting element is in the form of a bolt, the free end of which is threaded to screw into a bore in a post, the bolt passing through a clamp delimiting at least one gripping jaw in the form of a slot placed transversely with respect to the connecting element, the slot having opposed clamping faces open to a first external surface of the clamps and a second external surface of the clamp acting as a spring.

* * * * *